(12) United States Patent
DeWyse et al.

(10) Patent No.: US 8,505,397 B2
(45) Date of Patent: Aug. 13, 2013

(54) METHODS OF CHARACTERIZING ALUMINUM OXIDES

(75) Inventors: Michael J. DeWyse, Pinconning, MI (US); Qigui Wang, Rochester Hills, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 391 days.

(21) Appl. No.: 12/894,213

(22) Filed: Sep. 30, 2010

(65) Prior Publication Data

US 2012/0079900 A1   Apr. 5, 2012

(51) Int. Cl.
*G01N 33/00*  (2006.01)
*B22D 23/00*  (2006.01)

(52) U.S. Cl.
USPC .............................................. 73/866; 164/47

(58) Field of Classification Search
USPC ............................................... 73/866; 164/47
See application file for complete search history.

(56) References Cited

PUBLICATIONS

Partington et al., Self-Sustaining Oxidation of Liquid Aluminum and Its Alloys Containing Magensium and Silicon, J Mater. Sci. 33, pp. 2447-2455, 1998.
Ritchie, et al., Oxidation of a Dilute Aluminum Magnesium Alloy, Oxidation of Metals, vol. 3, No. 1, pp. 91-101, 1971.
Wang, et al., Oxide Films, Pores and the Fatigue Lives of Cast Aluminum Alloys, Metall. Mater. Trans. vol. 37B, pp. 887-895, 2006.

*Primary Examiner* — Hezron E Williams
*Assistant Examiner* — Gregory J Redmann
(74) *Attorney, Agent, or Firm* — Dinsmore & Shohl LLP

(57) ABSTRACT

Methods of characterizing aluminum oxide defects are described. The oxide defect type, as well as the time when the oxide defects are formed during the aluminum melting and casting processes can be identified quickly.

14 Claims, 12 Drawing Sheets

METHODS OF CHARACTERIZING ALUMINUM OXIDES

FIELD OF THE INVENTION

The present invention relates generally to methods of characterizing aluminum oxides and, more particularly, to methodologies and techniques to quickly determine when and where the aluminum oxides are formed during aluminum melting and casting process.

BACKGROUND OF THE INVENTION

Aluminum readily oxidizes in the presence of air (Eqn. (1)), or moisture (Eqns. (2 and 3)), rapidly forming a thin, strong protective oxide film on any exposed aluminum metal surface, including both liquid and solid surfaces.

$$4Al + 3O_2 \rightarrow 2Al_2O_3 \qquad (1)$$

$$3H_2O + 2Al \rightarrow Al_2O_3 + 3H_2 \qquad (2)$$

$$H_2 \rightarrow 2[H]_{melt} \qquad (3)$$

Because aluminum oxide is very stable thermodynamically, it is typically present in all aluminum alloys. Therefore, any furnace charge contains unavoidable amounts of alumina as a typical coating, constituting an exogenous inclusion source. During the mold filling of the casting process, aluminum oxides are formed when the free surface of the melt front contacts air and particularly when the liquid melt velocity produces turbulent flow. A distinction is often made between oxides pre-existing in the melting furnace, referred to as "old oxides," and those created during mold filling, called "young oxides." Campbell, J., *Castings*, Elsevier Butterworth-Heinemann, 2003; Q. G. Wang, C. J. Davidson, J. R. Griffiths, and P. N. Crepeau, "Oxide Films, Pores and The Fatigue Lives of Cast Aluminum Alloys", Metall. Mater. Trans. vol. 37B (2006), pp. 887-895. For young oxides, the cause of entrainment has been described as "surface turbulence," a reference to phenomena such as two or more flow fronts joining together (bifilm, flow marks, fold, and cold shut), a contraction of the surface area of a liquid (with folding of the oxide surface), or the passage of a bubble through the liquid.

Young oxides are more detrimental to material properties than old oxides. Because of the lack of wetting between oxide films folded dry side to dry side in young oxides, the entrained oxide unfurls during solidification and acts like a void or crack in the solidifying aluminum casting. These cracks can not only be initial sites for pore formation, but also be frozen into the solid and can significantly decrease the tensile and fatigue strengths of the casting. The bi-films can also cause hot tearing. Entrained oxides are believed to increase melt viscosity, and hence reduce fluidity, and adversely affect the feeding of castings. Surface oxide skins can significantly increase the apparent surface tension of melts and increase the possibilities of forming cold shut, flow marks, and misruns.

In order to minimize and eventually eliminate the oxides in the final cast aluminum products, it is desired to identify not only the oxide types, but also the time when they are formed particularly for young oxides in the casting process. This will help foundrymen to design and optimize gating/riser system, filtration, and fill profile more effectively.

Although there is a strong practical need for characterizing aluminum oxides, no reliable method or technique has yet been reported.

SUMMARY OF THE INVENTION

The present invention relates to methods of characterizing aluminum oxides and, more particularly, to methodologies and techniques to determine oxide types quickly and to determine the time when the aluminum oxides are formed during the aluminum melting and casting processes.

Two types of oxides, old and young, can be determined and differentiated in terms of their differences in morphology and chemical compositions. The old oxides, which pre-exist in the liquid melt during melting, are usually thick, flat, and dry on one side due to the complete unfurling process in melting. The young oxides, which are formed during mold filling, are relatively thin and tortuous (wrinkled) and are often present as bifilms. The young oxides are almost always associated with porosity. There is a clear difference in chemical compositions between old and young oxides. The oxygen and magnesium contents are higher in the old oxides compared with the young oxides. The Mg and O contents in the oxides increase with the exposure time of the oxides to an environment containing oxygen and Mg. Mg content is a better indicator for distinguishing between old and young oxides because it is easier to detect accurately.

The morphology, and in particular flatness (roughness and waviness), of the oxides can be evaluated on the fracture surfaces of the fractured samples using both qualitative and quantitative methods. The qualitative approaches include observing the oxides with either a stereo-microscope or a scanning electric microscope (SEM) and comparing the oxide images with standards in a database developed through this invention. The quantitative methods involve topographic measurements of the flatness (waviness) and roughness of the oxide surfaces. When the waviness and, in particular, the roughness is larger than one secondary dendrite arm spacing (SDAS), the oxides are considered to be young oxides.

The chemical composition of the oxides can be analyzed using energy dispersion spectrum (EDS) in a SEM or other analytical approaches, such as X-ray diffraction. When the Mg content is larger than 10%, and in particular larger than 15%, the oxides are old oxides. When the Mg content is larger than 5% but less than 10%, the young oxides were not folded but were retained on the melt free surfaces during mold fill, forming fold, cold shut, or misrun defects. When the Mg content is less than 5%, the young oxides are entrained during mold fill, and they can also be the result of bubble trail.

One aspect of the invention relates to a method of characterizing aluminum oxide defects in aluminum castings. In one embodiment, the method includes determining a magnesium content in the aluminum oxide defect; classifying the aluminum oxide defect as an old oxide if the magnesium content is greater than 10 wt %; and classifying the aluminum oxide defect as a young oxide if the magnesium content is 10 wt % or less.

In another embodiment, the method includes: determining a magnesium content in the aluminum oxide defect; determining a waviness and a roughness of the aluminum oxide defect; classifying the aluminum oxide defect as an old oxide formed during or prior to melting if the magnesium content is greater than 30 wt %; classifying the aluminum oxide defect as an old oxide formed in pouring ladle if the magnesium content is greater than 10 wt % up to 30 wt %; classifying the aluminum oxide defect as a type I young oxide—type I fold if the magnesium content is greater than 5 wt % up to 10 wt %, and the waviness is greater than 1 SDAS and less than 1 grain size, and the roughness is less than 1 SDAS; classifying the aluminum oxide defect as a type II young oxide type II fold, if the magnesium content is greater than 5 wt % up to 10 wt %, and the waviness is greater than 1 grain size, and the roughness is greater than 1 SDAS; classifying the aluminum oxide defect as a type III young oxide—cold-lap if the magnesium content is greater than 1 wt % up to 5 wt %, and the waviness is greater than 1 SDAS and less than 1 grain size, and the roughness is less than 1 SDAS; and classifying the aluminum oxide defect as a type IV young oxide—entrained bifilm if the magnesium content is less than 5 wt %, and the waviness is 1 SDAS or greater, and the roughness is greater than 1 SDAS.

Another aspect of the invention is a method of reducing aluminum oxide defects in an aluminum casting. In one embodiment the method includes: providing a mold with an initial mold design; melting aluminum in a furnace; casting the aluminum melt into the mold to form the aluminum casting; identifying an aluminum oxide defect in the aluminum part; determining a content of magnesium in the aluminum oxide defect; classifying the aluminum oxide defect as an old oxide if the magnesium content is greater than 10 wt %; classifying the aluminum oxide as a young oxide if the magnesium content is 10 wt % or less; and redesigning a melting process, a casting process, or both to reduce the amount of aluminum oxide defects in the aluminum casting.

DETAILED DESCRIPTION OF THE INVENTION

Figure 1:
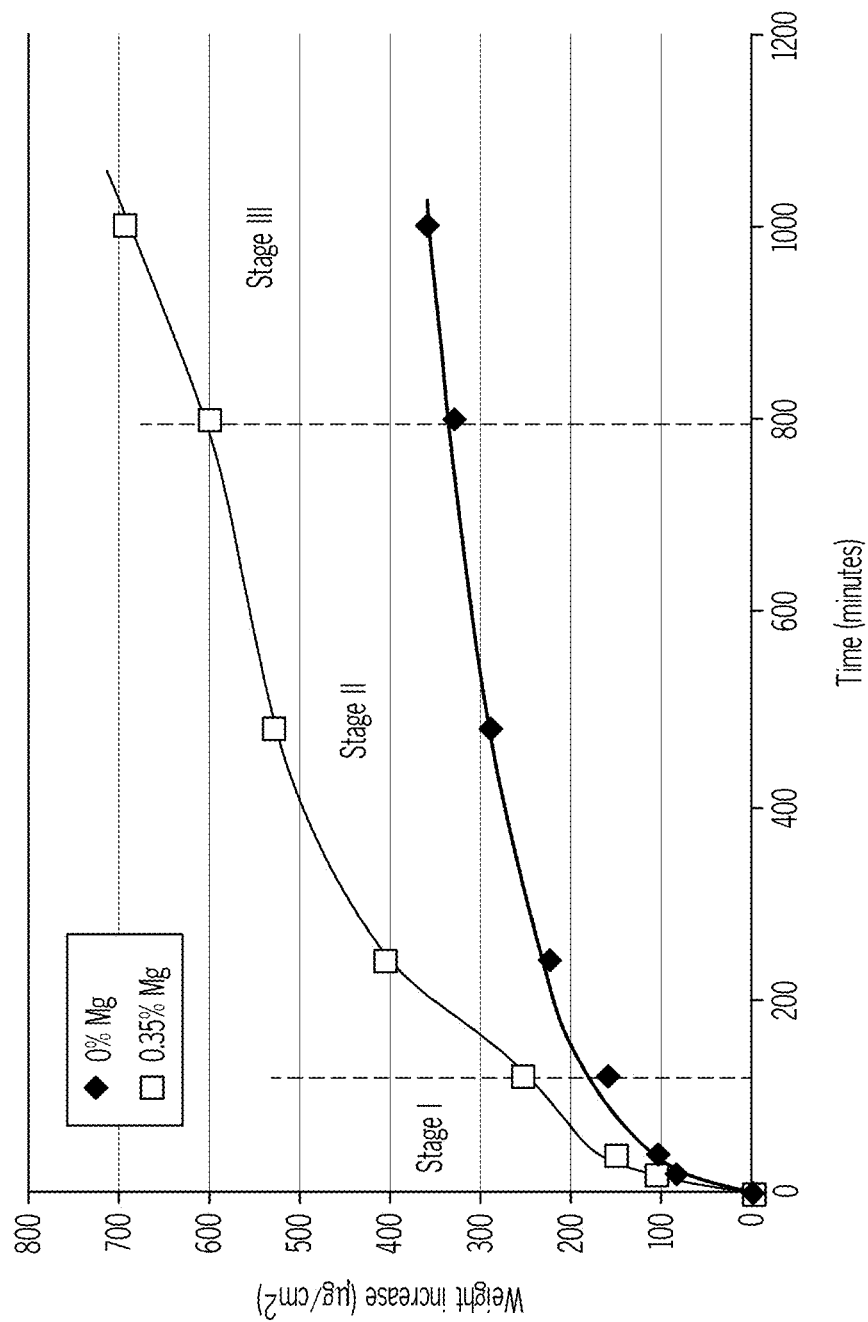
FIG. 1 is a graph showing the thermogravimetric analysis of the oxidation rate of aluminum alloy (Al-7 wt % Si) with a Mg content of 0% and 0.35 wt % at 730° C.

The oxides observed in aluminum castings can be readily identified using the methodologies and techniques of the present invention. The root causes of the various oxides can be easily determined, and solutions to minimize and eliminate them can be devised. A reduction in the amount of oxides not only reduces the oxide inclusions in the casting, but also decreases the porosity, and thus improves the casting quality and mechanical properties, as well as the reliability of the cast aluminum components.

The following characteristics can be summarized for various oxides. The old oxides are typically formed in the melting furnace, dipwell, launder, ladles, and pouring cups. They are flat and have high Mg content (greater than about 10 wt % to about 15 wt %). They appear dark with high carbon residue for the oxides observed in the lost foam casting. The old oxide inclusions are usually thick (e.g., ten to hundreds of micrometers, and up to 1-2 mm in some cases) and fracture at the interface between the aluminum matrix and the inclusions. The old oxide inclusions are mainly spinel ($MgAl_2O_4$).

The old oxides in the casting are caused by inclusions flowing into the casting from the melt, which thus have no preferred orientation and location in the casting. Unlike fold and cold-lap oxides, the old oxides have no indication of discontinuity that could be readily observed on the casting surface. There is no microstructure segregation associated with the old oxides in the casting.

Both fold and cold-lap oxides are formed during mold filling and are caused by converged melt fronts. Fold oxides appear to form at relatively high liquid melt temperature regions (thus they have high Mg content), whereas cold-lap oxides form at lower melt temperature regions (thus they have low Mg content) during mold fill. Fold oxides have double oxide films and fracture between the films. Cold-lap oxides are usually a single oxide film for each melt front. When two or more melt fronts meet, the melt fronts will not join together because of the meeting of the dry oxide surfaces. When stressed, the fracture will occur between the oxides of two or more melt fronts.

Fold oxides are usually close to a vertical orientation and are most likely attached to a bottom-facing casting surface. The cold-lap oxides do not show any preferred orientation. The cold-lap oxides usually appear smooth and dull with high carbon residue (in lost foam casting), whereas the fold oxides are more wrinkled and apt to be shiny.

The fold oxides tend to be planar and have very tight opening at the casting surface. The cold-lap oxides tend to be curved and exhibit some rounding on the casting surface. No difference in microstructure is expected between areas adjacent to and away from fold oxides, but there exists microstructure segregation with cold-lap oxides.

In lost foam casting, high carbon content can also be observed due to foam decomposition at the very top surface of the oxides. The carbon disappears after depth profiling to depth of about 0.5 μm. A metallographic approach can also be a very useful and convenient tool to analyze the old oxides and the fold/cold-lap/entrained young oxides in aluminum castings.

Oxidation of Aluminum Liquid

Figure 2:
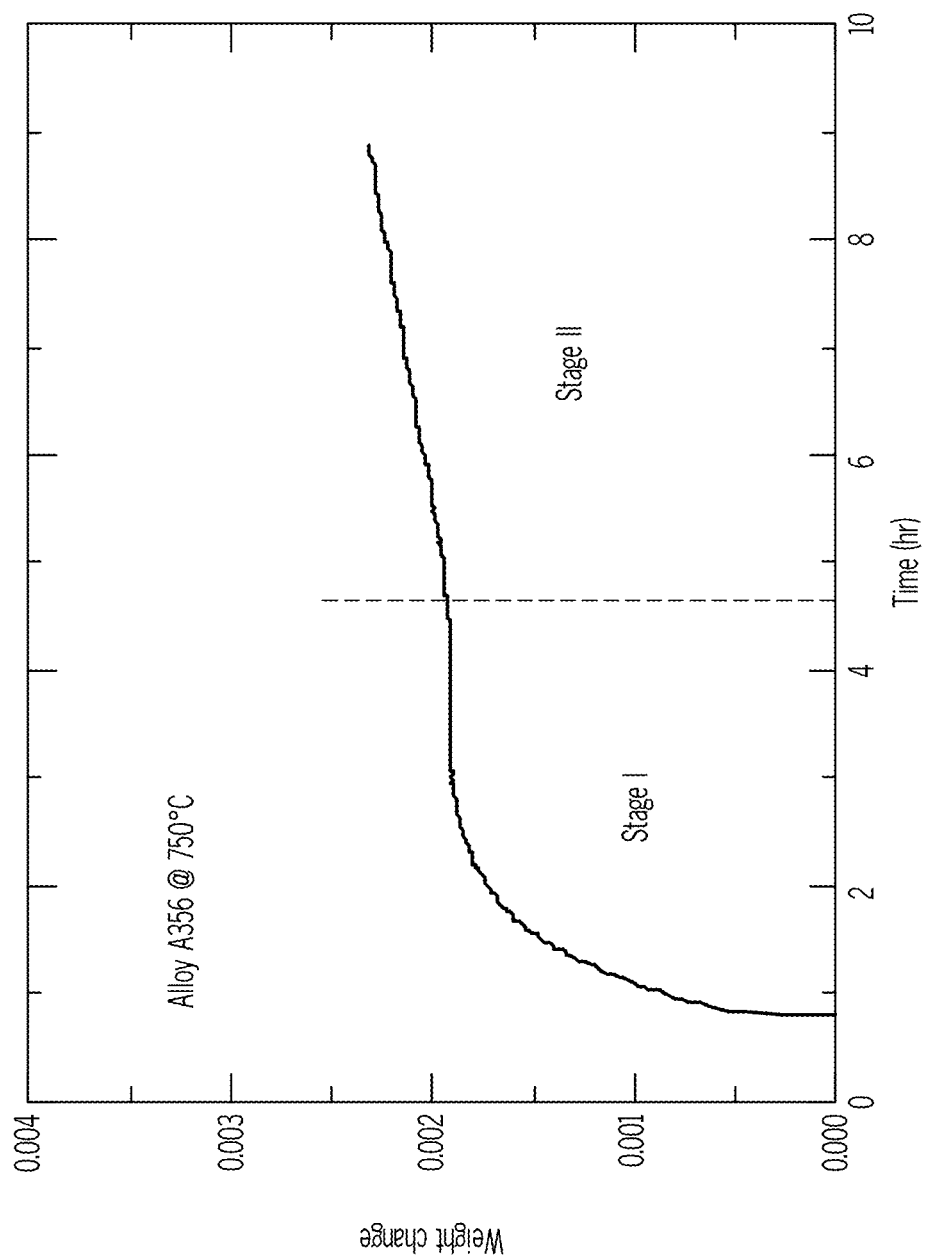
FIG. 2 is a graph showing the thermogravimetric analysis of the oxidation rate of an aluminum casting alloy A356 (Al-7% Si-0.4% Mg) at 750° C.

Aluminum oxide (either alpha, beta or gamma alumina) has an inherently strong protective effect. When any of the group IA or IIA oxides (except BeO) are present, however, the aluminum oxides are unable to maintain their continuous protection, particularly at elevated temperatures. In addition, more oxides and spinel form when the Mg content is greater than 0.005 wt % and the melt temperature is greater than about 745° C. When the aluminum alloy contains more than 0.5 wt % magnesium, in particular over 2 wt %, its oxidation process does not follow a typical parabolic law for pure aluminum. In contrast, MgO and/or spinel form almost exclusively, in addition to aluminum oxide, as shown in FIGS. 1 and 2. A significant number of commercially important casting and wrought aluminum alloys contain magnesium (e.g., A356, 319, A380, A390, A206, A6061, A6101, 530, etc.).

During the melting of these alloys, magnesium oxide and spinel continue to form regardless of whether surface film rupture occurs.

FIGS. 1 and 2 show the oxidation of aluminum liquid (weight change due to the increase of oxide layer on the aluminum liquid surface) with or without Mg at different holding temperatures. It can be seen that the oxidation process of aluminum liquid has at least three stages. Stage (I) involves the rapid formation of aluminum oxide ($Al_2O_3$) and possibly very small amount of magnesium oxide (MgO). After about 3 hrs, this barrier film was completely formed and no further oxidation occurred for the next one and one half hours. However, the protective layer did not last. The plateau ended about 4.5 hrs after the beginning of the plateau. Thereafter, the sample weight increased linearly. This indicates that the protective $Al_2O_3$ layer had been at least partially broken, leading to further oxidation of aluminum. It is believed that the second stage of oxidation was attributed to the formation of spinel $MgAl_2O_4$ and more $Al_2O_3$. The spinel layer prevents further oxidation of aluminum by forming a layer over the melt surface until channels are formed in it that produce flakes in the dross. Thereafter, the aluminum is further oxidized (stage III).

Thermodynamically, the only possible oxidation product at a given temperature is the one which lowers the free energy of the system by the largest amount under the conditions of the reaction. In aluminum alloys, Mg is differentially oxidized to form MgO and then reacts with $Al_2O_3$ to form spinel ($MgAl_2O_4$) through reactions (4)-(6).

M. Ritchie, J. V. Sanders, and P. L. Weiekhardt, "Oxidation of a Dilute Aluminum Magnesium Alloy", *Oxidation of Metals*, Vol. 3, No. 1 (1971) pp. 91-101, assumed that $\Delta G_{800}°$ for the formation of amorphous $Al_2O_3$ is approximately that for the formation of crystalline $\gamma$-$Al_2O_3$ and calculated the free energy changes for the following two reactions:

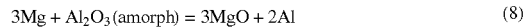

TABLE I

Reactions and Gibbs free energies of formation for $Al_2O_3$, MgO and $MgAl_2O_4$.

| Reactions | $\Delta G$ (KJ/kg) @ 750° C. |
|---|---|
| $Al + \frac{3}{4}O_2 = \frac{1}{2}Al_2O_3$ (5) | −217.5 |
| $Mg + \frac{1}{2}O2 = MgO$ (4) | −28.3 |
| $Mg + 2Al + 2O_2 = MgAl_2O_4$ (6) | −106.1 |
| $MgO + 2Al + \frac{3}{2}O_2 = MgAl_2O_4$ (9) | −77.7 |
| $MgO + Al_2O_3 = MgAl_2O_4$ (10) | −0.574 @ 520° C. |

Table I also lists the Gibbs free energy of some possible chemical reactions involving $Al_2O_3$, MgO and $MgAl_2O_4$ at a higher temperature. From the possible chemical reactions and free energy changes, it can be seen that spinel ($MgAl_2O_4$) is the stable oxidation product at temperatures above 800° K. During the initial oxidation stage, reaction (5) is dominant with a very minor contribution from reaction (4). Although reaction (10) may occur after the formation of MgO and $Al_2O_4$, it is very limited due to the higher Gibbs free energy compared with reactions (4) and (5). Reaction (6) may contribute to the formation of $MgAl_2O_4$ before a coherent $Al_2O_3$ layer is formed. Once $Al_2O_3$ film is formed, however, this reaction becomes unlikely. During early stage (II), reaction (5) is still dominant, but at a much slower rate and with more contributions from reaction (9) due to the increased MgO. Once more MgO and spinel ($MgAl_2O_4$) are formed, the preformed barrier layer ($Al_2O_3$ film) becomes no longer protective, and a rapid increase in oxidation rate occurs. The spinel layer prevents further oxidation of aluminum by forming a layer over the melt surface until channels are formed in it that produce flakes in the dross. After the spinel layer is broken, continuous oxidation of aluminum will take place (stage III). The chemical elements and various species involved with reactions (4)-(10) diffuse at a rapid rate to form a porous oxide at the surface and can dissociate at a later stage. Liquid alloys oxidize rapidly, and the reaction product grows outward from the original metal pool surface. This growth survives by the transport of liquid alloy elements through tortuous micro-channels in the oxide layer (known as wicking) to reach the oxide-gas interface. Alloying elements like magnesium improve the wettability of the liquid alloys during wicking, as does moisture. In aluminum alloys containing magnesium, magnesium is first oxidized at about 1025° K. The formation of magnesium oxide leads to about a 20% reduction in volume through the formation of a fragmented granular substance. Partington et al., "Self-sustaining oxidation of liquid aluminum and its alloys containing magnesium and silicon," J. Mater. Sci. 33, 2447-55, 1998. This disjointed product provides greater access to oxygen for the liquid alloy. The oxidation of alloys is accelerated at elevated temperatures, especially in the presence of locally heated regions known as hot spots.

The oxidation process of aluminum liquid (at high temperature) discussed above is similar to the observations reported by Ritchie et al. on a solid aluminum film oxidized at different temperatures. At lower temperatures (less than about 350° C.), the aluminum oxide formed is solely amorphous alumina. At temperatures greater than about 350° C., however, the diffraction patterns from the stripped oxide changed progressively with time of oxidation. Initially, the oxide was amorphous, then crystalline MgO was observed, followed by MgO and $MgAl_2O_4$ coexisting. At longer times of oxidation, only the spinel $MgAl_2O_4$ was detected.

Figure 3:
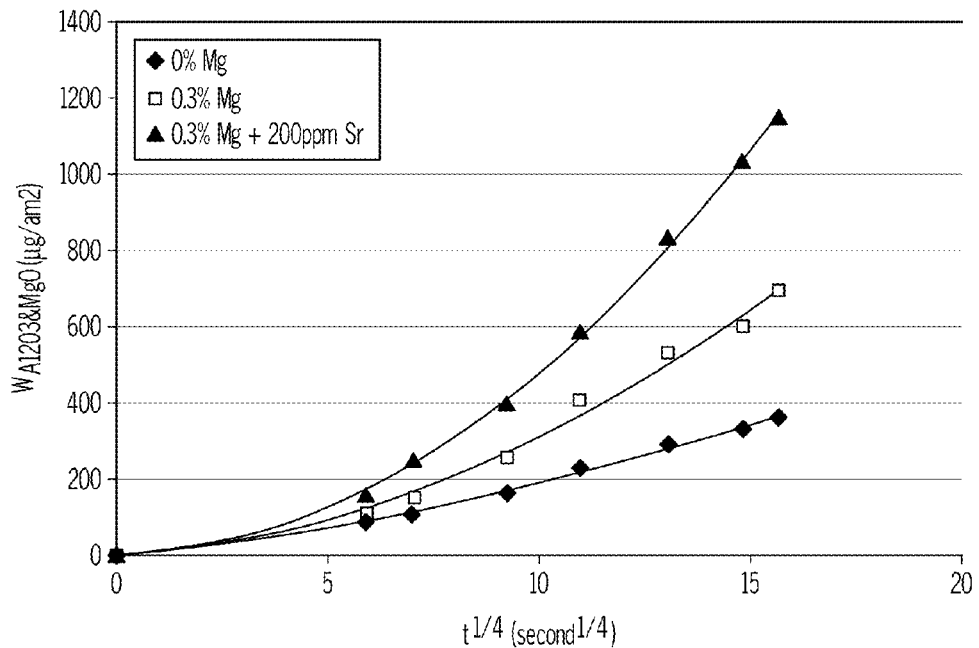
FIG. 3 is a graph showing the thermogravimetric analysis of the oxidation rate of aluminum casting alloys with 7 wt % Si with no Mg, with 0.35 wt % Mg, and with 0.35 wt % Mg and 200 ppm Sr at 730° C.

FIG. 3 shows the oxidation rate for an aluminum alloy containing 7 wt % Si at 730° C. When no Mg is present, the weight increase can be expressed by:

$$W_{Al_2O_3}=0.8169*t^{1/8}+10.815*t^{1/4}-3.2537 \quad (11).$$

When the Mg content is 0.35 wt %, the weight increase is the sum of Eqn. 11 and:

$$W_{Al_2O_3 \& MgO}=2.3426*t^{1/8}+8.5407*t^{1/4}-9.2559 \quad (12).$$

With 0.35 wt % Mg and 200 ppm Sr, the weight increase is the sum of Eqns. 11 and 12 and:

$$W_{Al_2O_3 \& MgO}=4.5582*t^{1/8}+3.2113*t^{1/4}-5.0514 \quad (13).$$

Figure 4:
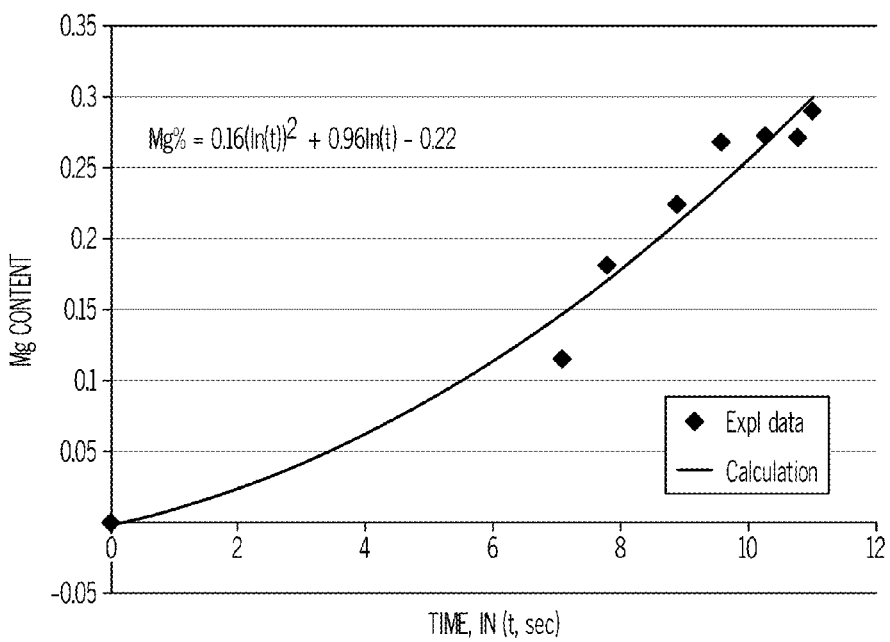
FIG. 4 is a graph showing the magnesium content in the aluminum oxides as a function of time of an aluminum casting alloy with 7 wt % Si as a function of time at 730° C.

FIG. 4 shows the Mg content in the aluminum oxides of an aluminum alloy with 7 wt % Si. The Mg content can be expressed as:

$$\text{Mg (wt \%)}=0.16(\ln(t))^2+0.96 \ln(t)-0.22 \quad (14).$$

Using this correlation, the measured Mg content in the oxides can be used to determine the time since the oxide was formed.

Differentiating Oxides Based on their Morphology and Appearance

Figure 5A:
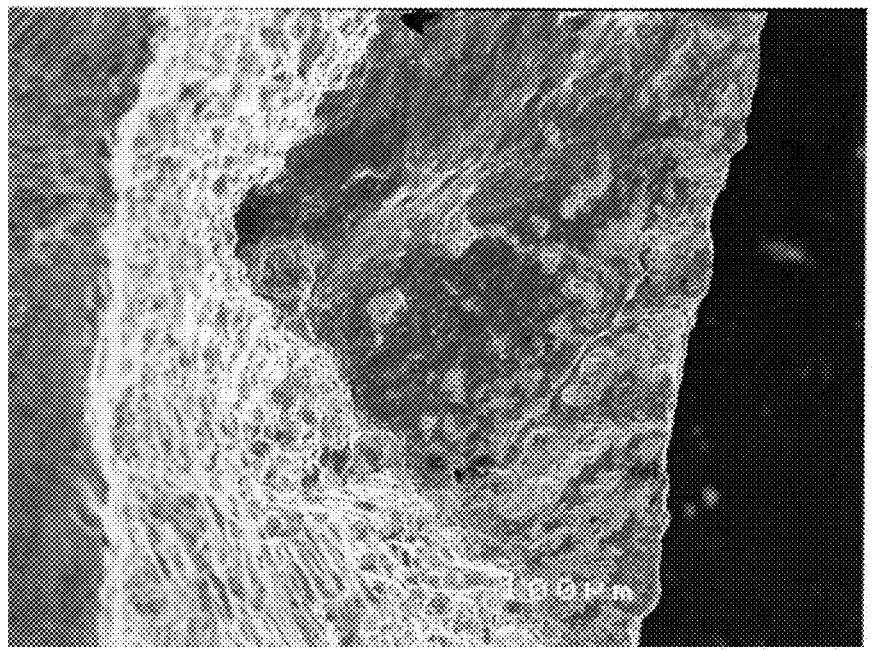
FIG. 5A is a SEM photograph showing an old oxide film observed in a sand cast A356 casting.
Figure 5B:
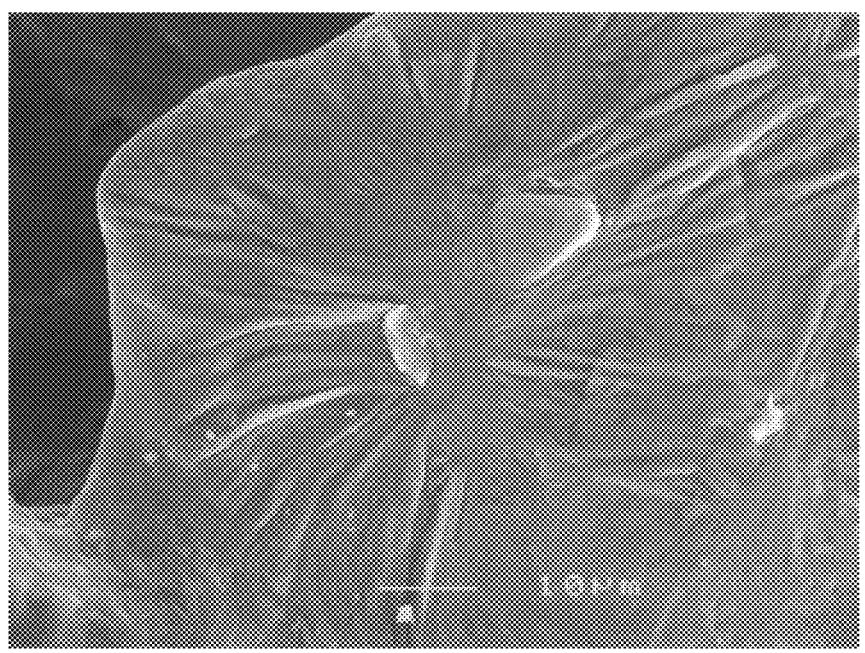
FIG. 5B is a SEM photograph showing a young oxide film that is associated with porosity.

As mentioned above, the oxide thickness and compositions vary with time. Increasing the exposure time of aluminum liquid to an oxygen and moisture containing environment increases the thickness of the oxides. The increased thickness increases the strength and stiffness of the oxides. The old oxide films are usually thicker and flatter in comparison with young oxides since the old oxides are formed during, or prior to, melting which can be as long as several hours or even several days. As a result, the old oxides tend to include the spinel and adsorbed contaminants. However, the young (new) films are predominantly pure $Al_2O_3$ and are formed during pouring and mold filling when freshly-exposed metal oxidizes. The length of pouring and/or mold filling time is relatively short, depending on the casting process and casting size, varying from milliseconds in high pressure die casting process to tens of seconds in sand casting. Turbulence during pouring doubles-over and entrains the surface oxides into the melt. Importantly, the double-folded oxide films often entrap air providing favorable nucleation sites for porosity. Therefore, the young oxides entrained in the castings are almost always associated with porosity. This is another distinguishing factor between the two types of oxides. FIG. 5 shows examples of both types of oxides observed in a sand cast A356 casting. Old oxide films (FIG. 5A) tend to be flatter and less convoluted than young films (FIG. 5B). The young oxide film is associated with porosity.

Oxide films are usually easy to detect under an optical microscope, but can sometimes be difficult to see under a scanning electron microscope. Thick films show charging effects in the secondary electron imaging mode, while thin, presumably fresh, films do not. In most cases, the young film splits and appears on both faces of the fractured specimen, showing that the film was folded and had not bonded to itself. When the young surface oxides are not folded over, however, due to high effective viscosity, low melt temperature, or low melt flow velocity and turbulence, the young oxides can be seen only on one face.

The morphology, and in particular flatness (roughness and waviness), of the oxides can be evaluated on the fracture surfaces of the fractured samples using both qualitative and quantitative methods. The qualitative approaches include observing the oxides with either a stereo-microscope or a scanning electric microscope (SEM) and comparing the oxide images with standards in a database developed through this invention. The quantitative methods involve topographic measurements of the flatness (waviness) and roughness of the oxide surfaces. When the waviness, and in particular the roughness, is larger than one SDAS, the oxides are considered to be young oxides.

Characterizing Oxides Based on their Chemical Compositions

As discussed above, there should be a clear difference in nano-scale lattice structure, microstructure, and chemical compositions between old and young oxides. As the old oxides are usually formed for a long time and thus contain spinel ($MgAl_2O_4$), the magnesium content in the old oxides should be much higher than that of the young oxides.

The chemical composition of the oxides can be analyzed using energy dispersion spectrum (EDS) in a SEM or other analytical approaches such as X-ray diffraction, inductively coupled plasma atomic emission spectroscopy (ICP-AES), attenuated total reflectance Fourier transform infrared (ATR-FTIR) spectroscopy, contact-mode atomic force microscopy (AFM), Auger electron spectroscopy (AES), and X-ray Photoelectron spectroscopy (XPS). When the Mg content is larger than 10 wt %, and in particular larger than 15 wt %, the oxides are old oxides. When the Mg content is larger than 5 wt % but less than 10 wt %, the young oxides were not folded but were retained on the melt free surfaces during mold fill, forming fold, cold shut, or misrun defects. When the Mg content is less than 5 wt %, the young oxides are entrained during mold fill, and they can also be the result of bubble trail.

Figure 6A:
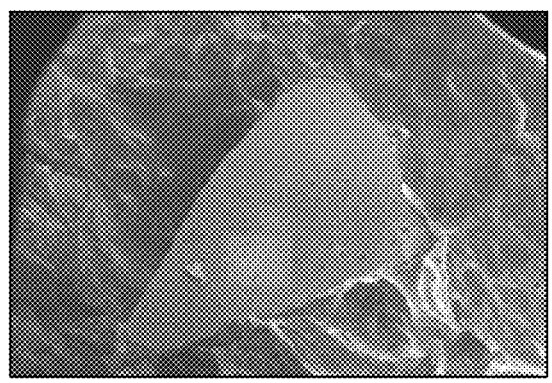
FIGS. 6A-B are SEM photographs showing an old oxide film observed in sand cast A356 casting.
Figure 6B:
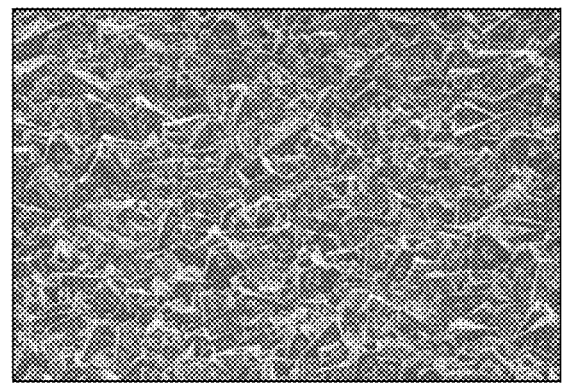
Figure 6C:
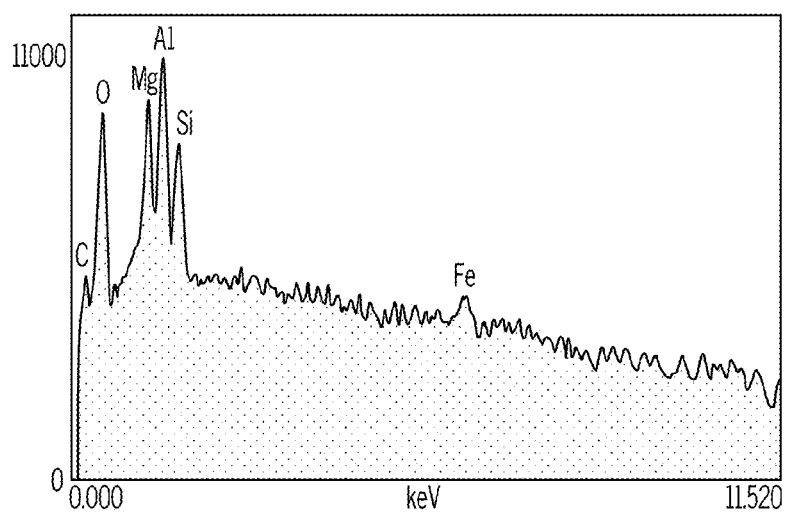
FIG. 6C is an EDS spectrum for the old oxide film.
Figure 7A:
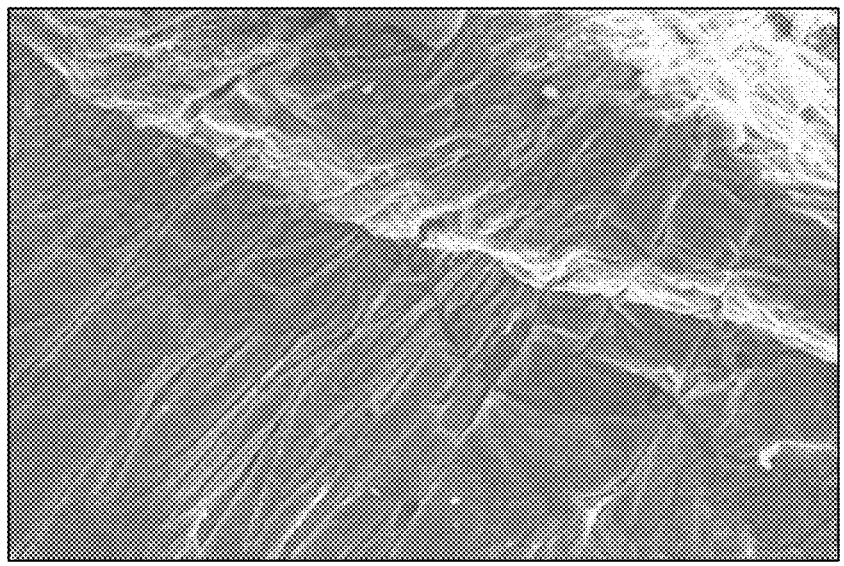
FIG. 7A is a SEM photograph showing a young oxide film observed in sand cast A356 casting.
Figure 7B:
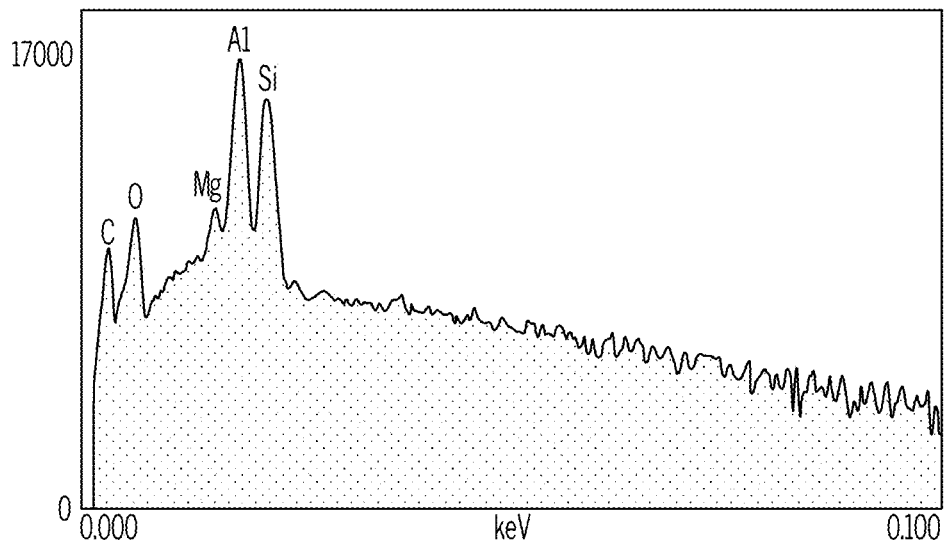
FIG. 7B is an EDS spectrum for the young oxide.

FIGS. 6 and 7 show examples of both types of oxides. The old oxide film (FIG. 6—observed in a sand cast A356 casting) formed in the dipwell furnace shows high Mg content and a clearly flat (FIG. 6A—low magnification image) and spinel (FIG. 6—high magnification image) morphology. Table 2 shows the chemical analysis from the EDS results of dross from the dipwell furnace (from FIG. 6C). The young oxide film (FIG. 7A—observed in the sand cast A356 casting) entrained in the casting during mold fill shows low Mg content and a clearly wrinkle morphology. Table 3 shows the EDS results of the fold (from FIG. 7B).

TABLE 2

| Elements | C | O | Mg | Al | Si | Fe |
|---|---|---|---|---|---|---|
| Atom % | — | 54.01 | 11.11 | 28.78 | 5.72 | 0.38 |
| Wt % | — | 41.3 | 12.9 | 37.11 | 7.68 | 1.02 |

TABLE 3

| Elements | C | O | Mg | Al | Si |
|---|---|---|---|---|---|
| Atom % | 15.73 | 8.91 | 1.05 | 46.21 28.78 | 28.09 |
| Wt % | 7.9 | 5.96 | 1.07 | 53.11 | 32.97 |

Categorizing Oxides

Figure 8A:
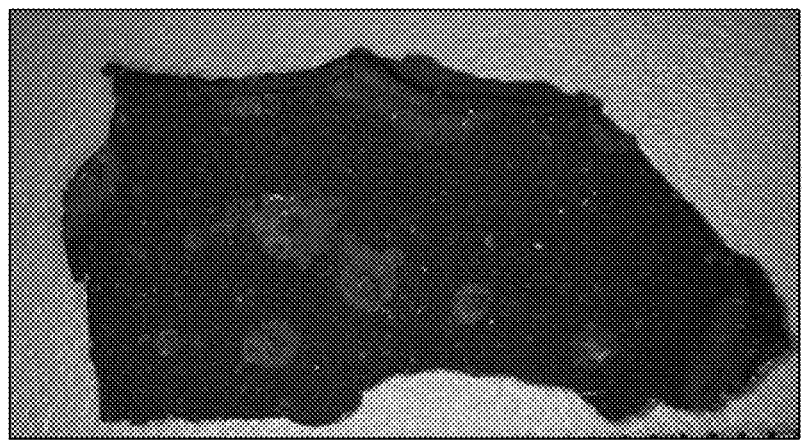
FIGS. 8A-B are SEM photographs showing type I old oxide.
Figure 8B:
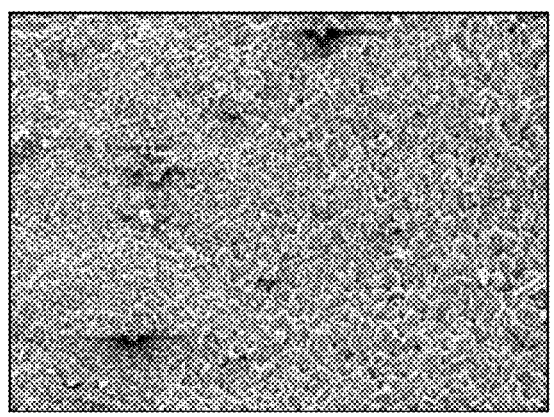
Figure 8C:
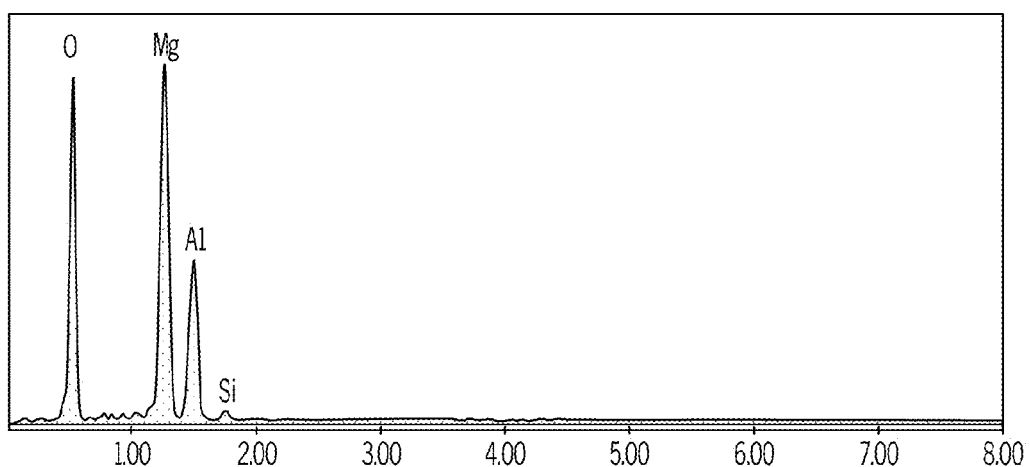
FIG. 8C is an EDS spectrum for type I old oxide.

FIGS. 8A-B show an old oxide (type I old oxide) formed during or prior to melting, and Table 4 shows the chemical analysis of this old oxide (from FIG. 8C). Type I old oxide had no measureable waviness and a measurable roughness of less than 1 SDAS. The Mg content is 38.08 wt %.

TABLE 4

| Elements | O | Mg | Al | Si |
|---|---|---|---|---|
| Atom % | 50.01 | 32.92 | 16.20 | 0.74 |
| Wt % | 38.01 | 38.08 | 21.30 | 1.01 |

Figure 9A:
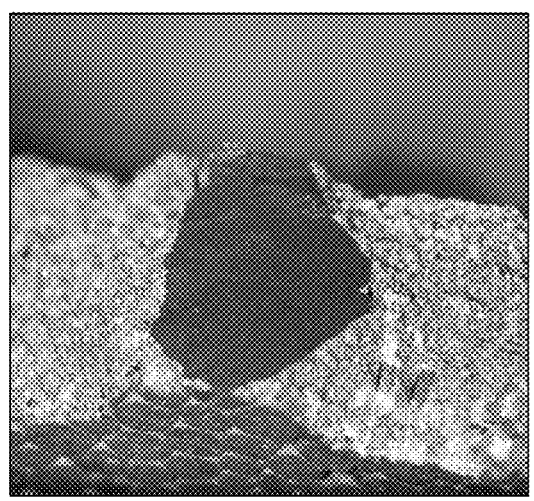
FIGS. 9A-B are SEM photographs showing type II old oxide.
Figure 9B:
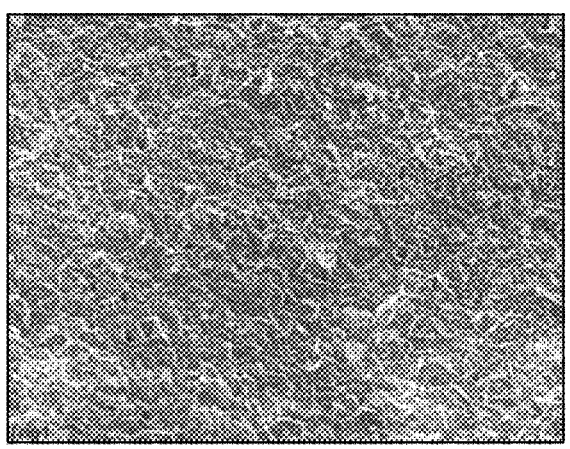
Figure 9C:
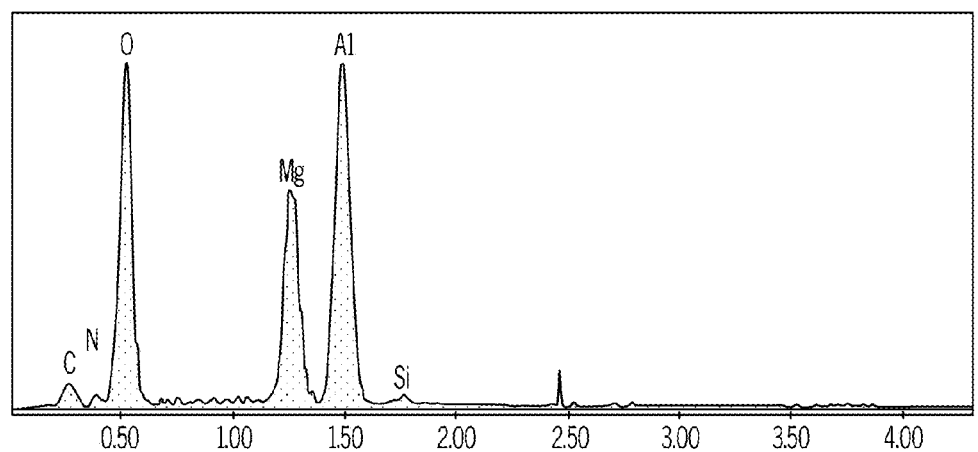
FIG. 9C is an EDS spectrum for type II old oxide.

FIGS. 9A-B show an old oxide (type II Old oxide) formed in the pouring ladle, and Table 5 shows the chemical analysis of this old oxide (from FIG. 9C). Type II Old oxide had no measurable waviness but the roughness is less than 1 SDAS. The Mg content is 17.54 wt %

TABLE 5

| Elements | C | N | O | Mg | Al | Si |
|---|---|---|---|---|---|---|
| Atom % | 15.84 | 3.76 | 43.92 | 13.66 | 22.231 | 0.51 |
| Wt % | 10.05 | 2.78 | 37.10 | 17.54 | 21.78 | 0.76 |

Figure 10A:
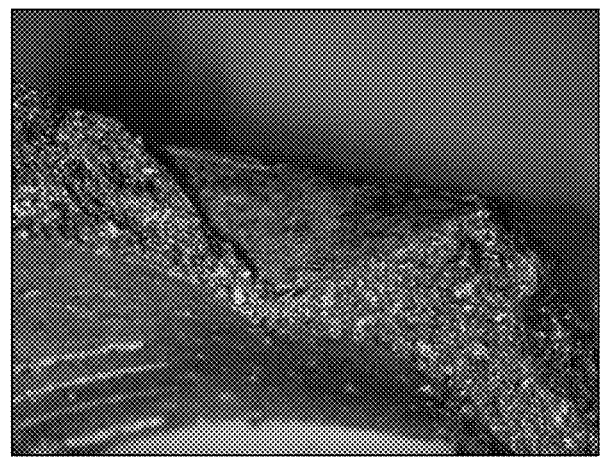
FIGS. 10A-B are SEM photographs showing type I young oxide.
Figure 10B:
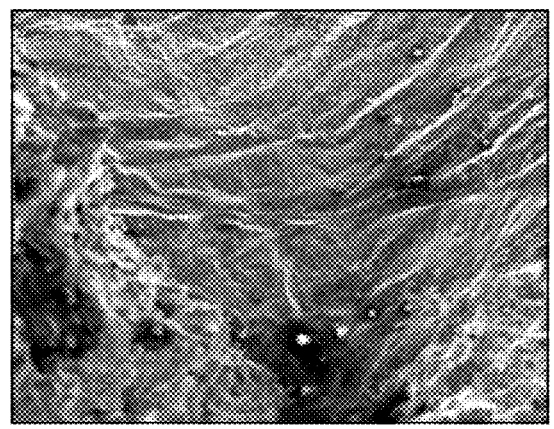
Figure 10C:
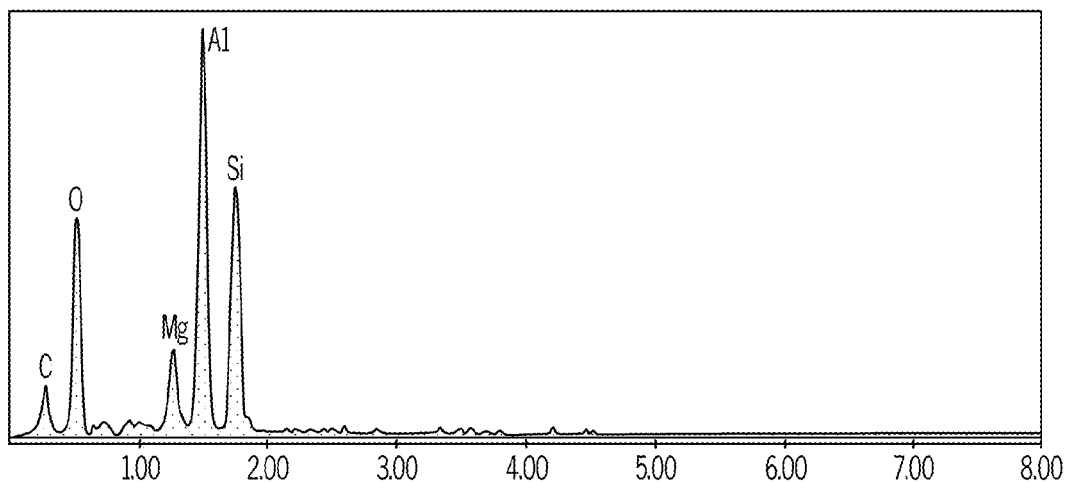
FIG. 10C is an EDS spectrum for type I young oxide.
Figure 11B:
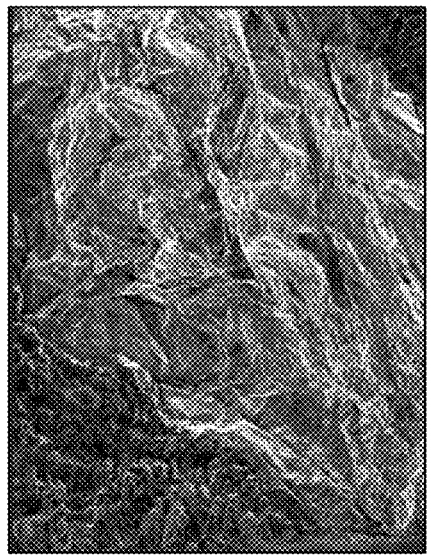
FIGS. 11A-D are SEM photographs showing type II young oxide.
Figure 11D:
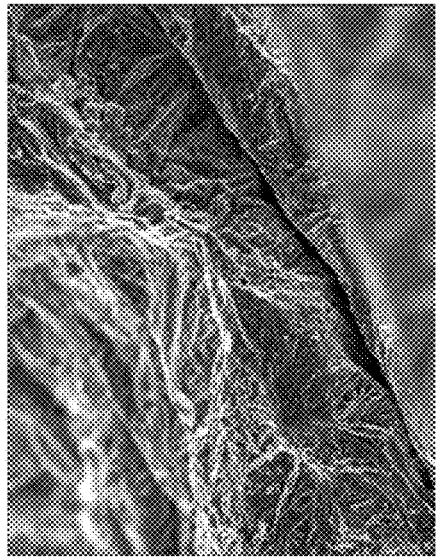
Figure 11A:
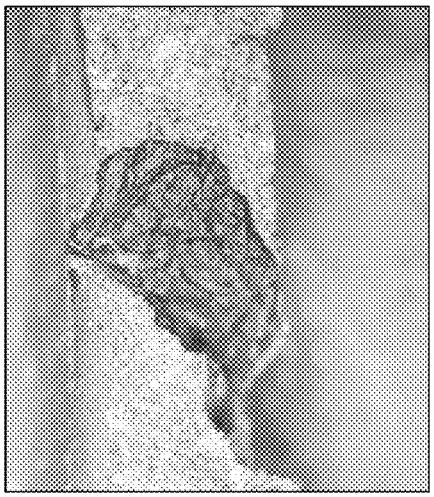
Figure 11C:
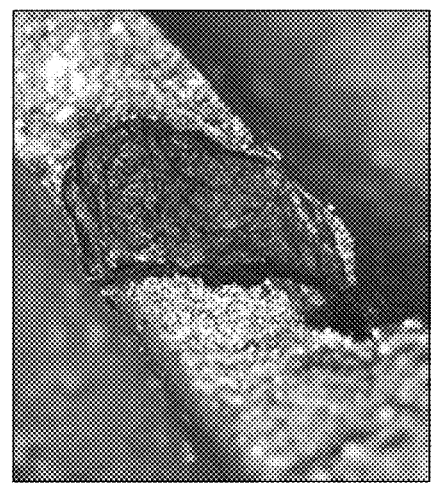

FIGS. 10A-B show a young oxide (Type I young oxide) type I folds in lost foam casting, and Table 6 shows the chemical analysis of this young oxide (from EDS results in FIG. 10C). Type I Young oxide—Type I folds had a waviness of greater than 1 SDAS and less than 1 grain size, and a roughness of less than 1 SDAS. The Mg content is 5.54 wt %.

TABLE 6

| Elements | C | O | Mg | Al | Si |
|---|---|---|---|---|---|
| Atom % | 31.37 | 28.34 | 4.38 | 20.02 | 15.89 |
| Wt % | 19.59 | 23.57 | 5.54 | 28.09 | 23.20 |

FIGS. 11A-B and 11C-D show two young oxides (type II young oxide) type II folds, and Tables 7-8 show the chemical analysis of these young oxides. Type II Young oxide—Type II folds had a waviness of greater than 1 grain size, and a roughness of greater than 1 SDAS. The Mg content is 5.21 wt % and 9.82 wt % respectively.

TABLE 7

| Elements | C | O | Mg | Al | Si |
|---|---|---|---|---|---|
| Atom % | 35.79 | 29.04 | 3.95 | 21.33 | 9.89 |
| Wt % | 23.31 | 25.20 | 5.21 | 31.22 | 15.06 |

TABLE 8

| Elements | C | O | Mg | Al | Si |
|---|---|---|---|---|---|
| Atom % | 31.03 | 37.64 | 7.31 | 17.44 | 6.58 |
| Wt % | 20.62 | 33.30 | 9.82 | 26.03 | 10.23 |

Figure 12A:
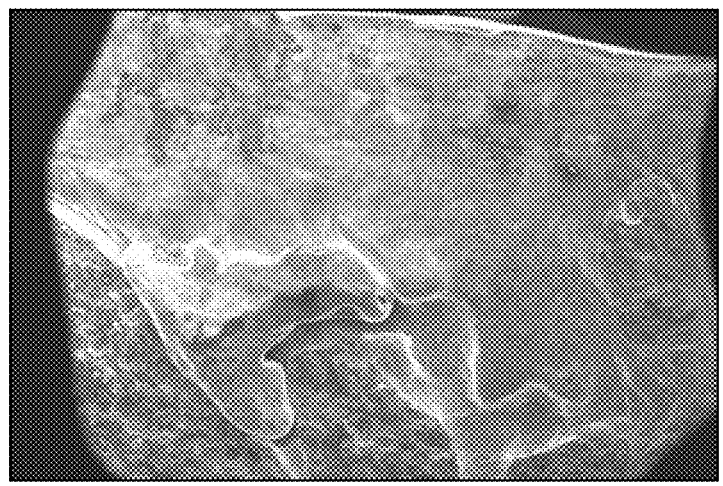
FIGS. 12A-B are SEM photographs showing type III young oxide.
Figure 12B:
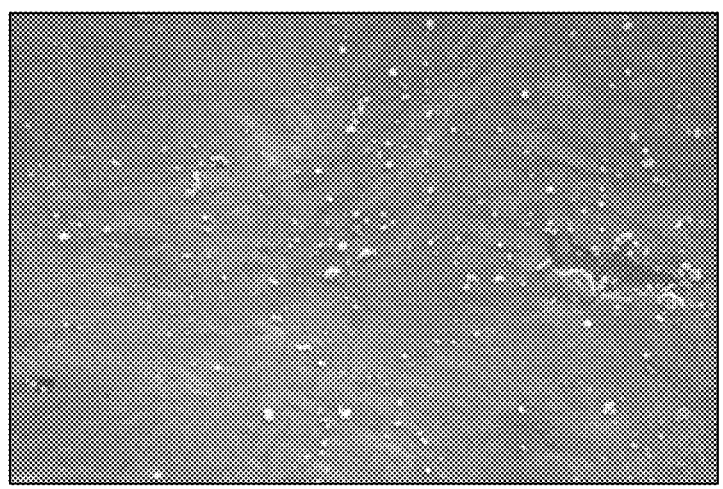

FIGS. 12 A-B show a young oxide (Type III young oxide)—cold-lap, and Table 9 shows the chemical analysis of this young oxide. Type III Young oxide—cold-lap had a waviness of greater than 1 SDAS and less than 1 grain size, and a roughness of less than 1 SDAS. The Mg content is 2.14 wt %.

TABLE 9

| Elements | C | O | Mg | Al | Si |
|---|---|---|---|---|---|
| Atom % | 29.23 | 16.47 | 1.85 | 23.63 | 28.47 |
| Wt % | 16.64 | 12.49 | 2.14 | 30.22 | 37.9 |

Figure 13A:
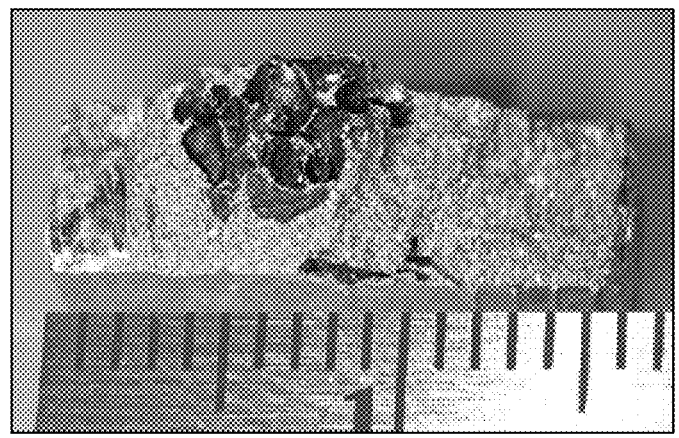
FIGS. 13A-B are SEM photographs showing type IV young oxide.
Figure 13B:
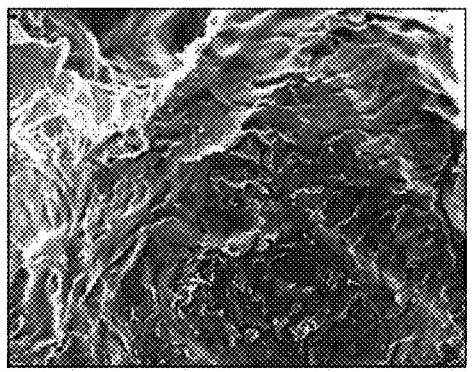
Figure 13C:
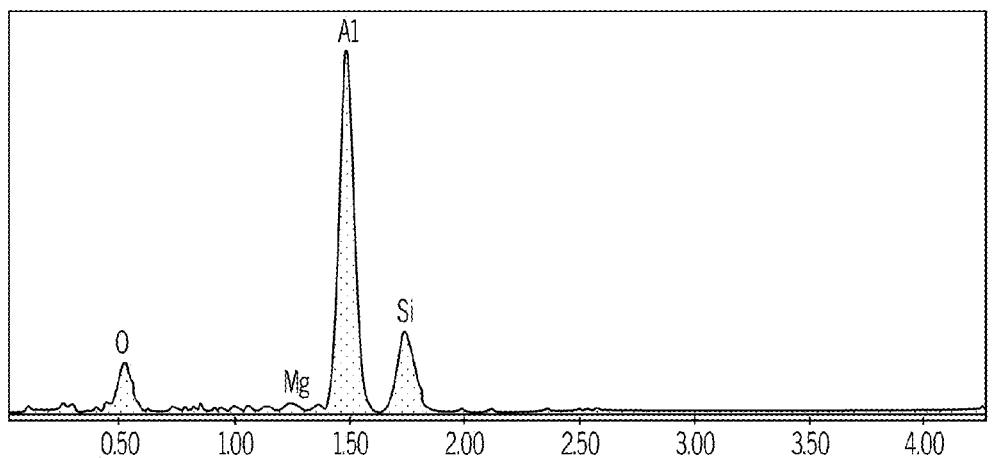
FIG. 13C is an EDS spectrum for type IV young oxide.

FIGS. 13 A-B show a young oxide (Type IV young oxide) entrained bifilm, and Table 10 shows the chemical analysis of this young oxide (from FIG. 13C). Type IV Young oxide—entrained bifilm had a waviness that varied from 1 SDAS to several grain sizes, and a roughness of greater than 1 SDAS. The Mg content is 5.54 wt %.

TABLE 10

| Elements | O | Mg | Al | Si |
|---|---|---|---|---|
| Atom % | 21.51 | 1.04 | 55.65 | 21.00 |
| Wt % | 13.88 | 1.80 | 60.55 | 23.70 |

According to the methods and approaches mentioned above, the aluminum oxides usually observed in cast aluminum components can be divided into the following categories.

(1) Type I Old oxide—Oxides formed during or prior to melting
   Waviness:—no measurable (flat plate)
   Roughness: <1 SDAS
   Mg: >30 wt %
(2) Type II Old oxide—oxides formed in pouring ladle
   Waviness:—no measurable (flat plane)
   Roughness: <1 SDAS
   Mg: >10 wt %
(3) Type I Young oxide—Type I folds in lost foam casting
   Waviness: >1 SDAS and <1 grain size
   Roughness: <1 SDAS
   Mg: >5 wt %
(4) Type II Young oxide—Type-II folds
   Waviness: >1 grain size
   Roughness: >1 SDAS
   Mg: >5 wt %
(5) Type III Young oxide—Cold-lap
   Waviness: >1 SDAS and <1 grain size
   Roughness: <1 SDAS
   Mg: 1 to about 5 wt %
(6) Type IV Young oxide—entrained bifilm
   Waviness: vary from 1 SDAS to several grain sizes
   Roughness: >1 SDAS,
   Mg: <5 wt %

If old oxides are found in a casting, it means that filtration needs to be enhanced to prevent old oxides formed in melting furnace from getting into the casting mold.

If young oxides are found in casting, it means that the gating/riser system design is not good. If it is known when the young oxides are formed during liquid melt flowing in the gating and riser system, the specific location and geometry of the gating/riser system can be optimized.

It is noted that terms like "generally," "commonly," and "typically," when utilized herein, are not utilized to limit the scope of the claimed embodiments or to imply that certain features are critical, essential, or even important to the structure or function of the claimed embodiments. Rather, these terms are merely intended to identify particular aspects of an embodiment or to emphasize alternative or additional features that may or may not be utilized in a particular embodiment.

For the purposes of describing and defining embodiments herein it is noted that the terms "substantially," "significantly," and "approximately" are utilized herein to represent the inherent degree of uncertainty that may be attributed to any quantitative comparison, value, measurement, or other representation. The terms "substantially," "significantly," and "approximately" are also utilized herein to represent the degree by which a quantitative representation may vary from a stated reference without resulting in a change in the basic function of the subject matter at issue.

Having described embodiments of the present invention in detail, and by reference to specific embodiments thereof, it will be apparent that modifications and variations are possible without departing from the scope of the embodiments defined in the appended claims. More specifically, although some aspects of embodiments of the present invention are identified herein as preferred or particularly advantageous, it is contemplated that the embodiments of the present invention are not necessarily limited to these preferred aspects.

What is claimed is:

1. A method of characterizing aluminum oxide defects in aluminum castings comprising:
   creating an oxide image with a scanning electron microscope;
   comparing said oxide image with a standard oxide image stored in a database;
   if an aluminum oxide defect exists:
      topographically measuring said oxide image with said scanning electron microscope;
      determining a magnesium content in the aluminum oxide defect using energy dispersion spectrum (EDS) with said scanning electron microscope;
      classifying the aluminum oxide defect as an old oxide if the magnesium content is greater than 10 wt %; and
      classifying the aluminum oxide defect as a young oxide if the magnesium content is 10 wt % or less;
      if said aluminum oxide defect is old, enhancing filtration between a melting furnace and a casting mold;
      if said aluminum oxide defect is young, optimizing a location and geometry associated with a gating/riser system into which a liquid melt flows prior to casting.

2. The method of claim 1 further comprising determining an actual oxide age based on Mg content using a formula:

$$Mg\ (wt\ \%) = 0.16(\ln(t))^2 + 0.96 \ln(t) - 0.22 \text{ where } t \text{ is the time (second)}.$$

3. The method of claim 1 further comprising classifying the old oxide as being formed in the pouring ladle if the magnesium content is greater than 10 wt % up to 30 wt %, and as being formed during or prior to melting if the magnesium content is greater than 30 wt %.

4. The method of claim 1 further comprising determining a waviness of a surface of the aluminum oxide defect, and classifying the aluminum oxide defect as a young oxide if the waviness is greater than 1 SDAS.

5. The method of claim 1 further comprising determining a roughness of a surface of the aluminum oxide defect, and classifying the aluminum oxide defect as a young oxide if the roughness is greater than 1 SDAS.

6. The method of claim 1 further comprising:
   determining a waviness and a roughness of the aluminum oxide defect;
   classifying the young oxide as type I young oxide—type I fold if the magnesium content is greater than 5 wt % up to 10 wt %, and the waviness is greater than 1 SDAS and less than 1 grain size, and the roughness is less than 1 SDAS;
   classifying the young oxide as type II young oxide—type II fold if the magnesium content is greater than 5 wt% up to 10 wt %, and the waviness is greater than 1 grain size, and the roughness is greater than 1 SDAS;
   classifying the young oxide as type III young oxide—cold-lap if the magnesium content is greater than 1 wt % up to 5 wt %, and the waviness is greater than 1 SDAS and less than 1 grain size, and the roughness is less than 1 SDAS; and
   classifying the young oxide as type IV young oxide—entrained bifilm if the magnesium content is less than 5 wt %, and the waviness is 1 SDAS or greater, and the roughness is greater than 1 SDAS.

7. A method of characterizing aluminum oxide defects in aluminum castings comprising:
   determining a magnesium content in the aluminum oxide defect using a technique selected from the group consisting of energy dispersion spectrum (EDS), X-ray Diffraction, inductively coupled plasma atomic emission spectroscopy (ICP-AES), attenuated total reflectance Fourier transform infrared (ATR-FTIR) spectroscopy, contact-mode atomic force microscopy (AFM), Auger electron spectroscopy (AES), and X-ray Photoelectron spectroscopy (XPS);
   determining a waviness and a roughness of the aluminum oxide defect by topographically measuring a surface of said aluminum oxide defect with a microscope;
   classifying the aluminum oxide defect as an old oxide formed during or prior to melting if the magnesium content is greater than 30 wt %;
   classifying the aluminum oxide defect as an old oxide formed in pouring ladle if the magnesium content is greater than 10 wt % up to 30 wt %;
   classifying the aluminum oxide defect as a type I young oxide—type I fold if the magnesium content is greater than 5 wt % up to 10 wt %, and the waviness is greater than 1 SDAS and less than 1 grain size, and the roughness is less than 1 SDAS;
   classifying the aluminum oxide defect as a type II young oxide—type II fold if the magnesium content is greater than 5 wt % up to 10 wt %, and the waviness is greater than 1 grain size, and the roughness is greater than 1 SDAS;
   classifying the aluminum oxide defect as a type III young oxide—cold-lap if the magnesium content is greater than 1 wt % up to 5 wt %, and the waviness is greater than 1 SDAS and less than 1 grain size, and the roughness is less than 1 SDAS; and
   classifying the aluminum oxide defect as type IV young oxide—entrained bifilm if the magnesium content is less than 5 wt %, and the waviness is 1 SDAS or greater, and the roughness is greater than 1 SDAS;
   if said aluminum oxide defect is classified as an old oxide, enhancing filtration between a melting furnace and a casting mold;
   if said aluminum oxide defect is classified as a young oxide, optimizing a location and geometry associated with a gating/riser system into which a liquid melt flows prior to casting.

8. The method of claim 7 further comprising determining an actual oxide age based on Mg content using a formula:

$$Mg\ (wt\ \%) = 0.16(\ln(t))^2 + 0.96 \ln(t) - 0.22 \text{ where } t \text{ is the time (second)}.$$

9. A method of characterizing aluminum oxide defects in aluminum castings comprising:
   determining a magnesium content in the aluminum oxide defect using energy dispersion spectrum (EDS) with said scanning electron microscope;
   classifying the aluminum oxide defect as an old oxide if the magnesium content is greater than 10 wt %; and
   classifying the aluminum oxide defect as a young oxide if the magnesium content is 10 wt % or less;
   if said aluminum oxide defect is old, enhancing filtration between a melting furnace and a casting mold;
   if said aluminum oxide defect is young, optimizing a location and geometry associated with a gating/riser system into which a liquid melt flows prior to casting.

10. The method of claim 9 further comprising determining an actual oxide age based on Mg content using a formula:

Mg (wt %)=0.16(ln($t$))$^2$+0.96 ln($t$)−0.22 where $t$ is the time (second).

11. The method of claim 9 further comprising classifying the old oxide as being formed in the pouring ladle if the magnesium content is greater than 10 wt % up to 30 wt %, and as being formed during or prior to melting if the magnesium content is greater than 30 wt %.

12. The method of claim 9 further comprising determining a waviness of a surface of the aluminum oxide defect, and classifying the aluminum oxide defect as a young oxide if the waviness is greater than 1 SDAS.

13. The method of claim 9 further comprising determining a roughness of a surface of the aluminum oxide defect, and classifying the aluminum oxide defect as a young oxide if the roughness is greater than 1 SDAS.

14. The method of claim 9 further comprising:
  determining a waviness and a roughness of the aluminum oxide defect;
  classifying the young oxide as type I young oxide—type I fold if the magnesium content is greater than 5 wt % up to 10 wt %, and the waviness is greater than 1 SDAS and less than 1 grain size, and the roughness is less than 1 SDAS;
  classifying the young oxide as type II young oxide—type II fold if the magnesium content is greater than 5 wt % up to 10 wt %, and the waviness is greater than 1 grain size, and the roughness is greater than 1 SDAS;
  classifying the young oxide as type III young oxide—cold-lap if the magnesium content is greater than 1 wt % up to 5 wt %, and the waviness is greater than 1 SDAS and less than 1 grain size, and the roughness is less than 1 SDAS; and
  classifying the young oxide as type IV young oxide—entrained bifilm if the magnesium content is less than 5 wt %, and the waviness is 1 SDAS or greater, and the roughness is greater than 1 SDAS.

* * * * *